(12) United States Patent
Mishkin et al.

(10) Patent No.: US 7,410,579 B2
(45) Date of Patent: Aug. 12, 2008

(54) MANUAL DIALYZER HEADER CLEANING DEVICE

(75) Inventors: Gary J. Mishkin, Potomac, MD (US); Mark A. Mishkin, Kensington, MD (US)

(73) Assignee: Alcavis International, Inc., Gaithersburg, MD (US)

( * ) Notice: Subject to any disclaimer, the term of this patent is extended or adjusted under 35 U.S.C. 154(b) by 0 days.

(21) Appl. No.: 11/028,550

(22) Filed: Jan. 5, 2005

(65) Prior Publication Data

US 2006/0144776 A1    Jul. 6, 2006

(51) Int. Cl.
*B01D 65/02* (2006.01)
*B08B 3/00* (2006.01)

(52) U.S. Cl. .................. 210/321.69; 134/167 R; 134/177; 210/636

(58) Field of Classification Search .......... 210/636, 210/646; 134/166 R, 167 R, 168 R, 172, 134/176, 177, 179
See application file for complete search history.

(56) References Cited

U.S. PATENT DOCUMENTS

| 1,897,981 | A | * | 2/1933 | Johnson ............... 15/229.11 |
| 2,778,503 | A | * | 1/1957 | White ................. 210/238 |
| 2,985,342 | A | * | 5/1961 | Focht ................. 222/402.24 |
| 4,375,413 | A |   | 3/1983 | Geel et al. |
| 4,559,138 | A | * | 12/1985 | Harms, II ............ 210/316 |
| 6,050,278 | A |   | 4/2000 | Arnal et al. |
| 6,823,881 | B1 | * | 11/2004 | Mishkin et al. ...... 134/167 R |

* cited by examiner

*Primary Examiner*—John Kim
(74) *Attorney, Agent, or Firm*—Browdy and Neimark

(57) ABSTRACT

A dialyzer header cleaning device composed of: a connecting member for connecting the device to the header, the connecting member having a longitudinal passage with a longitudinal axis; and a flow directing member having first and second opposed ends and a fluid passage extending between a fluid inlet at the first end and a fluid outlet at the second end. The flow directing member has a portion that extends from the second end toward the first end and is held in the longitudinal passage. The flow directing member is manually rotatable about the longitudinal axis relative to the connecting member and is manually movable along the longitudinal axis relative to the connecting member. The fluid outlet of the flow directing member is constructed to eject at least one liquid stream in a direction transverse to the longitudinal axis when fluid is supplied to the fluid inlet.

13 Claims, 1 Drawing Sheet

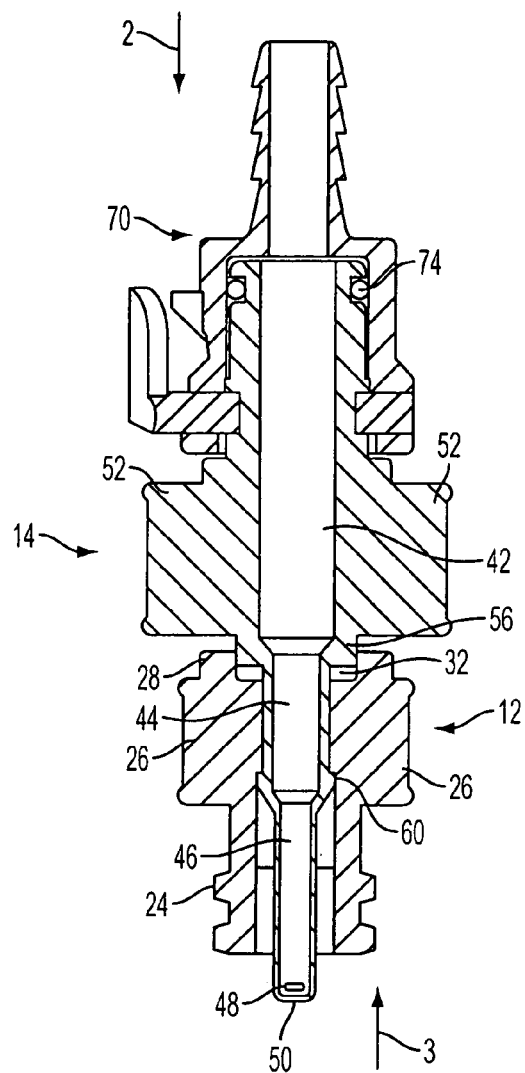
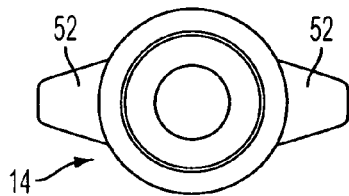
FIG. 2
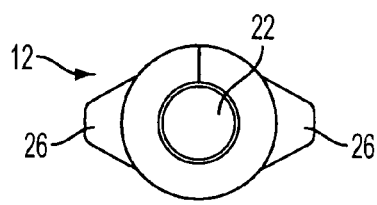
FIG. 3
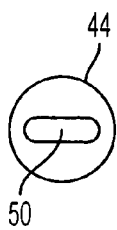
FIG. 4
FIG. 1

MANUAL DIALYZER HEADER CLEANING DEVICE

BACKGROUND OF THE INVENTION

The present invention relates to devices for cleaning dialyzer headers.

Hemodialysis is an extracorporeal therapy whereby blood is pumped out of the body and through a dialyzer, also know as an artificial kidney, and returned back to the body. The dialyzer is composed of two regions: a blood region and a dialysate region, the two regions being separated from one another by a filter-like membrane possibly composed of hollow fibers or flat sheets. The membrane is porous and permits water and small and middle weight molecules to pass across.

The blood that is pumped out of the body is pumped through the blood region of the dialyzer. Dialysate, a fluid that contains the electrolytes the body needs and bicarbonate to aid in acid base balance in the body, is caused to flow through the dialysate region in counter current to the blood flow through the blood region. Toxins in the blood pass across the membrane from the blood region into the dialysate region by diffusion or convection. Electrolytes and bicarbonate pass from the dialysate in the dialysate region across the membrane into the blood region in a similar manner.

Many dialysis facilities reuse the dialyzers in order to save money. The costs associated with dialyzer reuse include: reuse space, water and electricity, the cost of machines specifically designed to reprocess the dialyzers, reprocessing chemicals, and employee salaries.

The steps involved in dialyzer reuse vary from clinic to clinic. However, certain steps are universal. After completion of a dialysis treatment, the first step in the reuse process is to rinse any residual blood out of the dialyzer. For this purpose, the dialyzer is connected to a water supply and fluid is flushed through the blood and/or dialysate regions. This process rinses out many of the large particles and blood components left in the dialyzer. After the dialyzer is rinsed the dialyzer is then reprocessed.

Although many clinics throughout the world manually reprocess the dialyzers, there are currently many machines, such as those marketed by Alcavis International, Inc. under the trade name ARM, Minntech Corp. under the trade name Renatron, Mesa Medical under the trade name Echo, etc., that are capable of automatically reprocessing dialyzers.

Automatic reprocessing is similar to manual reprocessing. In automatic reprocessing, the dialyzer is connected to the reprocessing machine by both blood ports (arterial and venous) and both dialysate ports. Water or other cleaning liquid is then flushed through both regions of the dialyzer to further rinse away blood products. This is done in several steps. The cleaning step of dialyzer reprocessing is performed by flushing a cleaning solution through the dialyzer. This is also performed in other steps including a backflush. The backflush process rinses the water and cleaning agent from the dialysate side through the membrane to the blood region and out of the blood region ports. This backflush process can loosen and remove any blood or blood products that are adhered to the inner wall of the dialyzer fibers.

Most reused dialyzers are taken out of use, or fail, because the volume of the dialyzer, i.e., the volume of the blood compartment, has dropped below acceptable levels. Any blood products that block the fibers will reduce the volume of the dialyzer. Very rarely does a dialyzer fail due to inadequate results on a leak test.

The headers of a dialyzer are the parts of the dialyzer where the blood enters and leaves the dialyzer. During dialysis, as blood is pumped through the dialyzer, microclots, fibrin and other biologic products react with the dialyzer and may also react with the extracorporeal circuit consisting of blood lines, the pump and the dialysate compartment. These biologic products commonly accumulate in the headers of the dialyzer, many times forming a sheet that can completely block the openings to the fibers and blood region of the dialyzer.

These biologic products must be removed from the dialyzer in order to obtain adequate blood volume during reuse testing. Currently, flushing water is the most common method used to remove the biologic products from the header of the dialyzer. However, due to the design of the dialyzer header, this is not always effective. Some dialyzers have header caps that can be unscrewed to facilitate cleaning. However, due to concerns of cross contamination, the complexity of properly reassembling such a dialyzer and damage to the dialyzers, removing the header caps is discouraged.

U.S. Pat. Nos. 6,050,278 by Arnal et al and 4,375,413 by Geel et al disclose dialyzer cleaning devices having needles for injecting water into the dialyzer head. The device disclosed by Geel et al has a single solid piece for spraying water, which is not capable of rotating or retracting. Arnal et al disclose a needle that may oscillate and retract. Oscillation is effected by a gear assembly that undergoes reciprocal motion created by a pulsating fluid. Thus, this is a structurally complex device.

BRIEF SUMMARY OF THE INVENTION

The present invention provides a novel manually operated device that is structurally simple, and hence inexpensive, and that allows accurate control of the cleaning of dialyzer headers.

A dialyzer header cleaning device according to the invention is composed of: a connecting member for connecting the device to the header, the connecting member having a longitudinal passage with a longitudinal axis; and a flow directing member having first and second opposed ends and a fluid passage extending between a fluid inlet at the first end and a fluid outlet at the second end. The flow directing member has a portion that extends from the second end toward the first end and is held in the longitudinal passage. The flow directing member is manually rotatable about the longitudinal axis relative to the connecting member and is manually movable along the longitudinal axis relative to the connecting member. The fluid outlet of the flow directing member is constructed to eject at least one liquid stream of cleaning fluid, or solution, in a direction transverse to the longitudinal axis when fluid is supplied to the fluid inlet.

The cleaning solution can have any composition known or found to be suitable for cleaning a dialyzer header, such as, by way of nonlimiting examples, water or reverse osmosis water mixed with a cleaning agent such as a bleach or peroxyacetic acid, plain water, or reverse osmosis water alone.

BRIEF DESCRIPTION OF THE DRAWING

FIG. 1 is a cross-sectional view of a preferred embodiment of a dialyzer header cleaning device according to the invention connected to a coupler for connecting the device to a source of cleaning fluid.

FIG. 2 is an end view of a first member of the cleaning device according to the invention, taken in the direction of the arrow 2 of FIG. 1.

FIG. 3 is an end view of a second member of the cleaning device according to the invention, taken in the direction of the arrow 3 shown in FIG. 1.

FIG. 4 is an end view of the first member of the cleaning device according to the invention, taken in the direction of the arrow 3 shown in FIG. 1.

DETAILED DESCRIPTION OF THE INVENTION

The embodiment of a dialyzer header cleaning device according to the invention, shown in FIGS. 1-3, is composed of a connecting member 12 for connecting the device to a dialyzer header, and a flow directing member 14 for directing a fluid flow from a source of cleaning fluid into the dialyzer header.

Connecting member 12 is provided with a longitudinal passage 22 having a longitudinal axis and is formed to have a male thread for connection to a fluid passage in a dialyzer header (not shown). The structure of a dialyzer header and the manner in which a cleaning device is connected thereto is fully illustrated and described in copending allowed U.S. patent application Ser. No. 09/918,541, filed on Aug. 1, 2001, and entitled SINGLE CHANNEL, RETRACTABLE NEEDLE DIALYZER HEADER CLEANING DEVICE, now issued as U.S. Pat. No. 6,823,881. This application is incorporated herein by reference.

Member 12 is further provided with two laterally projecting parts, or wings, 26 that provide manual gripping surfaces for facilitating a connection of member 12 to the dialyzer header and to allow member 12 to be held in position while member 14 is rotated relative thereto, as will be described in greater detail below.

Member 12 is further provided, at the end thereof remote from thread 24, with an anular shoulder 28 that encloses a cylindrical recess 32 having a circular cross section.

Flow directing member 14 is provided with a longitudinal passage that has a first, inlet, end and a second, outlet, end. The inlet end is the upper end shown in FIG. 1. Starting from the inlet end, the fluid passage has a first portion 42, followed by a second portion 44, and finally a third portion 46. Portion 44 has a smaller diameter than portion 42 and portion 46 has a smaller diameter than portion 44. Tapered transitions are provided between successive portions. This arrangement produces successive increases in the velocity of fluid flow through the longitudinal passage and maximizes the volume of fluid passing through the device.

Portion 46 may have an essentially closed outlet end, with one, two, or more lateral openings, or nozzles, 48, each for ejecting a liquid stream in a direction transverse to, and preferably substantially perpendicular to, the common longitudinal axis of passage 22 and fluid passage 42, 44, 46. The liquid stream directions could be at a small angle to the perpendicular. Portion 46 may optionally be provided with a further opening, or nozzle, 50, at the outlet end for directing cleaning solution against the center of the dialyzer header.

Member 14 is further provided with two laterally projecting portions, or wings, 52 that facilitate rotation of member 14 relative to member 12. Below portions 52, member 14 is provided with a cylindrical portion 56 that fits into recess 32. As is visible in FIG. 1, portion 56 and recess 32 are dimensioned to allow limited longitudinal movement of member 14 relative to member 12, for example in the range of 1 to 3 mm.

In addition, members 12 and 14 are provided with a detent arrangement 60 that serves to retain members 12 and 14 in the assembled condition shown in FIG. 1 during use, while allowing the members to be separated, for example to facilitate cleaning. FIG. 1 illustrates the relative positions of members 12 and 14 when member 14 is at the upper end of its path of movement relative to member 12 during a cleaning operation. Further upward movement would overcome the detent action and allow members 12 and 14 to be separated. However, it would be possible to construct the members so that, once assembled, they cannot be separated.

The upper end of member 14 is constructed to be connected to a standard coupling element 70, for example of the quick connect type, that is connected to a source of cleaning fluid. Coupling element 70 could be constructed, for example, as a "Quick Coupling" system of the type marketed by Colder Products Corp., or as a conventional luer structure. In more general terms, coupling element 70 may have any standard construction. To provide a suitable sealed connection, member 14 may be provided with an O-ring seal 74.

To use the device, member 12 is screwed into a dialyzer header and member 14 is connected to coupling element 70. A cleaning fluid supply tube is installed on element 70 and a flow of cleaning fluid is produced. While the cleaning fluid is being ejected in a stream(s) from outlet(s) 48, member 14 may be rotated manually, by acting on wings 52, in order to rotate the stream(s) around the longitudinal axis of the fluid passage in flow directing member 14. During this cleaning operation, member 14 may also be moved longitudinally relative to member 12, also by manual operation, so that portion 56 is displaced longitudinally within recess 32. This produces a longitudinal displacement of the cleaning fluid stream(s) in order to ensure that the cleaning fluid reaches all surfaces at the interior of the header. It may be desirable to form openings 48 so as to angle the fluid streams upwardly to facilitate cleaning of the header end surface.

After cleaning one side of the dialyzer, the dialyzer should be flipped over and the other header cleaned. This will also push clots and bio debris from the first header out into the sink. It would then be advantageous to again flip the dialyzer to rinse the debris out of the second header as well.

When cleaning is completed, the flow of cleaning fluid is halted and member 12 is disconnected from the header. Thereafter, members 12 and 14 may be separated to facilitate cleaning.

While each member 12, 14 is shown as being made in one piece, each of them could be made of several parts that are bonded together.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

Thus the expressions "means to . . . " and "means for . . . ", or any method step language, as may be found in the specification above and/or in the claims below, followed by a functional statement, are intended to define and cover whatever structural, physical, chemical or electrical element or structure, or whatever method step, which may now or in the future exist which carries out the recited function, whether or not precisely equivalent to the embodiment or embodiments disclosed in the specification above, i.e., other means or steps for carrying out the same functions can be used; and it is intended that such expressions be given their broadest interpretation.

What is claimed is:

1. A dialyzer header cleaning device comprising:

a connecting member for connecting said device to a dialyzer header, said connecting member having a longitudinal passage with a longitudinal axis; and a flow directing member having first and second opposed ends and a fluid passage extending between a fluid inlet at said first end and a fluid outlet at said second end, wherein:

said flow directing member has a portion that extends from said second end toward said first end and that is held by said connecting member in said longitudinal passage;

said flow directing member is manually rotatable about said longitudinal axis relative to said connecting member to control the direction of fluid flow from said fluid outlet;

said fluid outlet of said flow directing member is constructed to eject at least one liquid stream in a direction transverse to said longitudinal axis when fluid is supplied to said fluid inlet; and said flow directing member comprises two laterally projecting parts for facilitating manual rotation of said flow directing member relative to said connecting member, said two laterally projecting parts being exposed and manually accessible to a user when said device is connected to the dialyzer header and is in operation to eject the at least one liquid stream into the dialyzer header.

2. The device of claim 1, wherein said flow directing member is manually movable along said longitudinal axis relative to said connecting member.

3. The device of claim 1, wherein said fluid outlet of said flow directing member is constructed to eject two liquid streams in respectively different directions transverse to said longitudinal axis.

4. The device of claim 3, wherein the directions of the two liquid streams are diametrically opposite one another.

5. The device of claim 1, wherein said connecting member and said flow directing member are provided with detent elements for allowing said flow directing member to be movable by a limited distance along said longitudinal axis relative to said connecting member.

6. The device of claim 5, wherein said second end of said flow directing member projects out of said connecting member.

7. The device of claim 1, wherein said connecting member comprises two laterally projecting parts for facilitating relative rotation of said members.

8. The device of claim 1, wherein said flow directing member is constructed, at said first end, for connection to a source of cleaning fluid.

9. The device of claim 1, wherein said flow directing member is a one-piece member.

10. The device of claim 1, wherein said second end of said flow directing member projects out of said connecting member.

11. The device of claim 1, wherein said fluid passage has first, second and third portions having respective cross sections that decrease from said fluid inlet to said fluid outlet, a first tapered transition between said first and second portions, and a second tapered transition between said second and third portions.

12. The device of claim 1, wherein said flow directing member has a further fluid outlet disposed to eject at least one liquid stream in a direction substantially parallel to said longitudinal axis when fluid is supplied to said fluid inlet.

13. The device of claim 1, wherein said two laterally projecting parts of said flow directing member are constituted by wings.

* * * * *